United States Patent [19]
Blase et al.

[11] Patent Number: 5,272,137
[45] Date of Patent: Dec. 21, 1993

[54] AQUEOUS PHARMACEUTICAL SUSPENSION FOR PHARMACEUTICAL ACTIVES

[75] Inventors: Cynthia M. Blase, Lansdale; Manoj N. Shah, Norristown, both of Pa.

[73] Assignee: McNeil-PFC, Inc., Milltown, N.J.

[21] Appl. No.: 835,877

[22] Filed: Feb. 14, 1992

[51] Int. Cl.$^5$ .................. A61K 9/10; A61K 31/715; A61K 47/36; A61K 47/38

[52] U.S. Cl. ..................... 514/54; 514/57; 514/159; 514/263; 514/289; 514/317; 514/327; 514/359; 514/570; 514/777; 514/781; 514/782; 514/819; 514/849; 514/850; 514/853; 514/854; 514/855; 514/974

[58] Field of Search ............... 514/54, 974, 849, 850, 514/853, 854, 855, 781, 782, 777, 819, 57, 159, 263, 289, 317, 327, 359, 570

[56] References Cited

U.S. PATENT DOCUMENTS

| | | | |
|---|---|---|---|
| 4,145,440 | 8/1977 | Fitch et al. | 514/975 |
| 4,361,580 | 5/1981 | Peck et al. | 514/975 |
| 4,427,681 | 1/1984 | Munshi | 514/849 |
| 4,711,774 | 12/1987 | Denick et al. | 424/683 |
| 4,716,033 | 12/1987 | Denick | 514/770 |
| 4,717,565 | 3/1987 | Demick | 514/974 |
| 4,761,274 | 10/1987 | Demick et al. | 514/974 |
| 4,766,216 | 8/1988 | Wright | 546/7 |
| 4,772,724 | 9/1988 | Wright et al. | 548/403 |
| 4,788,220 | 11/1988 | Mody et al. | 514/557 |
| 4,822,876 | 4/1989 | Wright et al. | 514/819 |
| 4,882,324 | 11/1989 | Wright et al. | 514/569 |
| 4,886,669 | 12/1989 | Ventouras | 424/469 |
| 4,895,723 | 1/1990 | Amer et al. | 514/974 |
| 4,923,981 | 5/1990 | Weibel et al. | 536/56 |
| 4,975,465 | 12/1990 | Motola et al. | 514/557 |
| 4,996,222 | 2/1991 | Carlia et al. | 514/400 |
| 5,013,557 | 5/1991 | Tai | 424/493 |
| 5,019,591 | 5/1991 | Gardner et al. | 514/648 |
| 5,024,997 | 6/1991 | Motola et al. | 514/974 |
| 5,032,393 | 7/1991 | Douglas et al. | 514/974 |
| 5,167,964 | 12/1992 | Muhammad et al. | 424/482 |

OTHER PUBLICATIONS

Remington's Pharmaceutical Sciences, 18th Ed., Chapter 83, Solutions, Emulsions, Suspensions and Extracts, pp. 1519-1530 (1990).

Primary Examiner—Ronald W. Griffin

[57] ABSTRACT

The present invention relates to an aqueous pharmaceutical suspension composition comprising: from about 0.2% to 20% of a substantially water soluble pharmaceutical active, e.g. acetaminophen; a suspension stabilizing effective amount of xanthan gum and microcrystalline cellulose; an effective amount of taste masking compositions; and water, as well as a process for producing such aqueous pharmaceutical suspensions.

12 Claims, No Drawings

AQUEOUS PHARMACEUTICAL SUSPENSION FOR PHARMACEUTICAL ACTIVES

FIELD OF THE INVENTION

This invention relates to aqueous suspensions. In one aspect, this invention relates to a pharmaceutical suspension composed of pharmaceutical actives, suspension agents, sweetening agents and flavoring agents. Another aspect of this invention provides a process for making aqueous pharmaceutical suspensions.

BACKGROUND OF THE INVENTION

Orally administered drugs are provided to the patient in many dosage forms, including solid forms such as capsules, caplets or tablets and liquid forms such as solutions, emulsions or suspensions. Pharmaceuticals administered in solid form are usually intended to be swallowed whole. Often the disagreeable taste of a drug does not need to be considered in formulating swallowable tablets or capsules. Because these dosage forms are in the mouth such a short time the pharmaceutical's taste can easily be masked with an exterior coating on the tablet.

Children, older persons, and many other persons including disabled or incapacitated patients often have trouble swallowing tablets or capsules. In these situations, it is desirable to provide the drug either in a chewable solid form or a liquid form. For many patients, including pediatric and geriatric patients, a liquid oral dosage form is preferable to a chewable dosage form. A liquid dosage is preferable for this class of patients because of the ease with which it may be swallowed. Additionally, patients may be more inclined to comply with their medication instruction if the dosages are easier to ingest.

However, a common problem associated with liquid pharmaceutical dosage forms is the often disagreeable taste of a drug that may manifest itself when the drug is in a liquid dosage form. Sometimes, the taste of the drug in the dosage form may be overpowered by adding sweeteners or flavoring agents to the liquid dosage. These agents mask the bitter or unpleasant taste of drugs. However, these agents are not totally effective in concealing the unpalatable taste of pharmaceuticals.

Liquid suspension dosage forms also have stability problems associated with maintaining the drugs in suspension. Poorly formulated liquid pharmaceutical suspensions allow the drug to settle out as a sediment, thereby reducing the therapeutic concentration of drug in the suspension. This results in under dosing or over dosing of the patient, which may seriously compromise the patient's recovery.

Additionally the pharmaceutical suspension should be readily pourable so that the dosage is easy to administer. The requirement that a pharmaceutical suspension is readily pourable effectively places an upper limit on the viscosity of the suspension. This limitation also indirectly limits the amount of pharmaceutical actives that the suspension will suspend.

In view of these difficulties it would be desirable to develop a ready-to-use pharmaceutical suspension with a high degree of stability and good taste masking characteristics. Therefore, there exists a need for a suspension system for pharmaceutical actives that minimizes sedimentation of the active ingredients and provides a pleasant tasting liquid dosage.

The present invention discloses a stable aqueous suspension system for pharmaceutical actives, which can be combined with sweeteners and flavoring agents to provide a palatable liquid dosage form. This dosage form is also physicochemically stable and especially well suited for both geriatric and pediatric applications.

SUMMARY OF THE INVENTION

The present invention provides a pharmaceutical suspension comprising a therapeutic amount of a drug; a suspending system consisting essentially of an effective amount of xanthan gum and microcrystalline cellulose to form a stable suspension system in an aqueous solution; water; and optionally an effective amount of sweetening agents and flavoring agents to provide a palatable taste to said pharmaceutical suspension.

Another embodiment of this invention provides a method for forming an aqueous suspension consisting essentially of dispersing microcrystalline cellulose in an aqueous solution to form a liquid dispersion; dispersing xanthan gum in a liquid solution to form a second liquid dispersion; admixing said first and second liquid dispersions to form an aqueous suspension, wherein the concentration of microcrystalline cellulose and xanthan gum in the aqueous suspension are in the range of from about 0.5 to about 1.0 grams of microcrystalline cellulose per 100 mL of aqueous suspension and in the range of from about 0.1 to about 0.2 grams of xanthan gum per 100 mL of the aqueous suspension.

DETAILED DESCRIPTION OF THE INVENTION

The present invention provides a novel suspension system particularly well suited for use in pharmaceutical suspensions. It is the applicants' discovery that a stable and pourable suspension can be formed by combining xanthan gum and microcrystalline cellulose in specific ratios.

Further, we have also discovered that this suspension can be employed in pharmaceutical suspensions to enhance the taste masking of unpalatable pharmaceutical actives. We have found that by limiting the amount of water in our suspension, the amount of pharmaceutical active dissolved in the suspension can be reduced. This reduction in amount dissolved reduces the need for taste masking. Since, the pharmaceutical active remains in the solid (undissolved) form, the pharmaceutical is less likely to be tasted while in the mouth.

The xanthan gums suitable for use in the present invention are high molecular weight polysaccharide produced by *Xanthamonas campestris*. Techniques and strains for producing this polysaccharide are described in U.S. Pat. No. 4,752,580 and U.S. Pat. No. 3,485,719 (the disclosures of which are hereby incorporated by reference). The xanthan gum used in the present invention should have a viscosity in a one percent salt solution of from about 1000 to about 1700 cP (mPa·sec.). The one percent solution's viscosity should be measured at 25° C. with an LV model Brookfield Synchro-Lectric viscometer at 60 rpm, no. 3 spindle. Xanthan gum is available from several commercial suppliers such as R. T. Vanderbilt Company and Kelco, a division of Merck. Examples of suitable xanthan gums are Keltrol TM, Keltrol TM F, Keltrol TM T, Keltrol TM TF and Keltrol TM 1000 (Keltrol is a trademark of Merck Inc.). Keltrol TM, Keltrol TM TF and Keltrol TM 1000 are the xanthan gums preferred for use in pharmaceutical suspensions.

The microcrystalline cellulose used in the present invention is a dried coprecipitated microcrystal of cellulose and carboxymethyl cellulose. Sodium carboxymethyl cellulose is commonly used as the coprecipitate in microcrystalline cellulose. It is presently preferable that carboxymethyl cellulose comprise in the range of from about 8 weight percent to about 19 weight percent of the total weight of the microcrystalline cellulose. Presently preferred are microcrystalline cellulose products having in the range of from about 8 to about 14 weight percent sodium carboxymethyl cellulose. Microcrystalline cellulose as described above is commercially available from FMC under the trademark Avicel TM CL-611, Avicel TM RC-581 and Avicel TM RC-591. Avicel TM RC-591 is the preferred microcrystalline cellulose product for use in pharmaceutical suspensions.

The suspension system described above forms a very stable and pourable suspension when the aqueous suspension contains in the range of from about 0.2 to about 0.12 grams xanthan gum per 100 mL of suspension and in the range of from about 1.0 to about 0.6 grams microcrystalline cellulose per 100 mL of suspension. Currently it is preferred that the weight ratio of xanthan gum to microcrystalline cellulose is maintained in about a 1:5 ratio. Preferably the amount of xanthan gum and microcrystalline cellulose in an aqueous suspension will be in the range of from 0.13 to 0.15 grams of xanthan gum per 100 mL of suspension and in the range of from 0.65 to 0.75 grams of microcrystalline cellulose per 100 mL of suspension.

The suspension system discussed above is suitable for suspending a variety of particulate solids in aqueous solutions. The particulate solids as a general guideline should have a particle diameter in the range of from about 1 micron to about 850 microns. Preferably the particle diameter will range from about 37 microns to about 420 microns (400 to 40 mesh based on U.S. standard mesh screens). However, those skilled in the art will recognize the fact that particle size of a specific particulate solid should be varied with the density of the particulate solid following the guidelines of Stokes' Law. The optimum particle size for a suspension should be determined empirically based on the end use and desired stability of the suspension.

The preferred pH of the suspension should range from about 4 to about 10. Preferably the pH of the suspension will be in the range of from 4 to 8. The suspension can be buffered to maintain the pH of the suspension in the desired pH range. Suitable buffers that are not chemically reactive with the other ingredients may be present in the suspension in amounts sufficient to provide the desired degree of pH buffering. Preferably the buffers will be present in the range of from 0 to 1 gram per 100 mL of the suspension.

The suspensions also may contain one or more of the following additives: wetting agents, defoaming agents, surfactants, buffers, electrolytes (monovalent cations are currently preferred), preservatives, colorings, flavorings, sweeteners, and sequestering agents.

The suspension previously described is also well suited for use in the formulation of pharmaceutical suspension. The following pharmaceutical actives are suitable for use with the inventive suspension including but not limited to acetaminophen, ibuprofen, famotidine, pseudoephedrine, hydrochloride, chlorpheniramine maleate, astemizole (sold under the trademark Hismanal by Janssen Pharmaceutica Inc.), dextromethorphan hydrobromide, guaifenesin, diphenhydramine hydrochloride, loperamide hydrochloride, simethicone and antacids (such as magnesium oxide, magnesium carbonate, magnesium hydroxide, magnesium trisilicate, magaldrate, aluminum hydroxide and calcium carbonate) and suitable combinations thereof.

Therapeutic combination of these pharmaceutical actives include but are not limited to combination of acetaminophen, ibuprofen or famitadine with pseudoephedrine hydrochloride, chlorpheniramine maleate, astemizole, terfenadine, dextromethorphan hydrobromide, guaifenesin or diphenbydramine for formulations of cold or sinus medication. Acetaminophen, ibuprofen and famitadine could also be combined with antacids to control the gastric irritation caused by these analgesics. Other combinations for treating gastric conditions are also possible such as combining simethicone with loperamide or one or more antacids.

The suspension system may contain up to about 40 grams of a pharmaceutical active per 100 mL of suspension. The amount of pharmaceutical active present in the suspension should be sufficient to provide a therapeutic amount of the active and a convenient dosage unit. Up to about 20 grams pharmaceutical active per 100 mL may be readily taste masked with the addition of sweeteners and flavoring agents. However, this may vary depending on the palatability of the pharmaceutical active.

The inventive suspension can effectively mask the bitter taste of pharmaceuticals contained in the suspension. Masking the flavor of bitter pharmaceuticals may be accomplished by using flavoring agents and sweeteners to overpower the bitter flavor of the pharmaceutical. The bitter flavor also can be minimized by limiting the amount of water present in the suspension. Suitable sweetening agents include but are not limited to sugars such as monosaccharides, disaccharides and polysaccharides. Examples of suitable sugars include but are not limited to xylose, ribose, glucose, mannose, galactose, fructose, dextrose, sucrose, maltose, partially hydrolyzed starch or corn syrup, and sugar alcohols such as sorbitol, xylitol, mannitol, glycerin and combination thereof. Presently preferred as a sugar sweetener is high fructose corn syrup provided as an aqueous solution. The amount of sugar sweetener used in the suspension will vary depending on the degree of sweetening desired for the particular suspension. Generally the amount of sugar sweetener will be in the range of from about 0 grams to about 85 grams sugar sweetener per 100 mL of the suspension. Preferably the amount of sugar sweetener will be in the range of from about 40 grams to about 85 grams per 100 mL of suspension. Water soluble artificial sweeteners also may be employed in place of or in addition to sugar sweeteners. Examples of suitable artificial sweeteners include but are not limited to aspartame, sucralose, cyclamates, saccharin and mixtures thereof. The amount of artificial sweetener used in the suspension may vary from in the range of 0 grams to about 5 grams artificial sweetener per 100 mL of suspension.

Flavoring agents also may be added to the suspensions to improve the palatability of the suspension. Examples of suitable flavoring agents include natural and artificial flavors such as mints (i.e., peppermint, etc.,), menthol, cinnamon, vanilla, artificial vanilla, chocolate, artificial chocolate, both natural and artificial fruit flavors (i.e., cherry, grape, orange, strawberry, etc.,) and combinations of two or more thereof. Flavoring agents are generally provided as a minor component of the suspension in amounts effective to provide a palatable flavor to the suspension. However, flavoring agents are generally present in the suspension in amounts in the range of from about 0 grams to about 5 grams per 100 mL of the suspension.

Optimum masking of the taste of the pharmaceutical actives in the suspension can be achieved by limiting the amount of water in the suspension. As a minimum, the amount of water present in the suspension may be limited to that amount necessary to hydrate the microcrystalline cellulose. The minimum amount of water also must provide the suspension with a sufficient aqueous base to impart the desired degree of viscosity. For example, if high fructose corn syrup is used in the suspension as a sweetener the aqueous component of the corn syrup could provide the necessary water to hydrate the microcrystalline cellulose. It is currently preferred for taste masking of bitter pharmaceuticals that the total amount of water contained in the suspension be in the range of from about 30 to 55 grams per 100 mL of suspension. Accordingly, if a bitter or unpalatable pharmaceutical active is present in the suspension, the amount of water in all the ingredients should be kept to a minimum.

Wetting agents also may be employed in the inventive suspension to facilitate the dispersion of hydrophobic pharmaceutical actives. The concentration of wetting agents in the suspension should be selected to achieve optimum dispersion of the pharmaceutical active within the suspension with the lowest feasible concentration of wetting agent. It should be appreciated that an excess concentration of wetting agent may cause the suspension to flocculate. Those skilled in the art are well versed in suitable empirical methods to determine the appropriate wetting agents and concentrations to achieve optimum dispersion and avoid flocculation. Suitable wetting agents are listed in the U.S. Pharmacoepia XXI.

Preservatives useful in the present invention include but are not limited to sodium benzoate, potassium sorbate, salts of edetate (also know as salts of ethylenediaminetetraacetic acid, or EDTA, such as disodium edetate) and parabens (such as methyl, ethyl, propyl and butyl p-hydroxybenzoic acids esters). The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art. Sodium Benzoate and butylparaben are the presently preferred preservative ingredients to add to a pharmaceutical suspension containing acetaminophen although other pharmaceutically acceptable preservatives may be substituted therefor.

Preservatives are generally present in amounts of up to gram per 100 mL of the suspension. Preferably the preservatives will be present in amounts in the range of from about 0.15 to about 0.5 grams per 100 mL of the suspension. For pharmaceutical suspensions containing acetaminophen it is currently preferred that the preservative sodium benzoate be present in the range of from about 0.15 to about 0.3 grams per 100 mL of the suspension and butylparaben be present in the range of from about 0.01 to about 0.05 grams per 100 mL of the suspension. It is most preferred that sodium benzoate be present at a concentration of 0.2 grams per 100 mL of the suspension and butylparaben be present at a concentration of 0.025 grams per 100 mL of the suspension.

Coloring agents also may be incorporated in the suspension to provide an appealing color to the suspension. The coloring agents should be selected to avoid chemical incompatibilities the other ingredients in the suspension. Suitable coloring agents for use in pharmaceutical suspensions are well know to those skilled in the art.

As one embodiment of the present invention, hereinafter is provided a pharmaceutical suspension containing acetaminophen. The following formulation of an acetaminophen containing pharmaceutical suspension provides a stable suspension that is pourable and has superior taste masking characteristics:

TABLE 1

Pharmaceutical Suspension of Acetaminophen[1,2]

| | Broad Range (grams) | Preferred Range (grams) |
|---|---|---|
| Xanthan Gum | 0.1–0.2 | 0.13–0.15 |
| Microcrystalline Cellulose | 0.5–1 | 0.65–0.75 |
| Acetaminophen | 1–15 | 8–12 |
| High Fructose Corn Syrup[3] | 20–80 | 60–75 |
| Sorbitol Solution USP[4] | 1–30 | 15–25 |
| Glycerin USP | 1–20 | 8–12 |
| Flavoring | 0.01–0.5 | 0.01–0.1 |
| Purified Water USP | 10–30 | 15–25 |
| Coloring | 0.003–.0005 | 0.0005–0.002 |
| Sodium Benzoate NF | 0.1–0.3 | 0.15–0.3 |
| Butylparaben | 0.01–0.05 | 0.02–0.03 |
| Citric Acid USP | 0.05–0.18 | 0.06–0.12 |

[1] All measurements in this table are listed in grams per 100 mL of suspension at measured at 25° C. If the volume of all the components does not equal 100 mL, the additional volume may be provided by the addition of high fructose corn syrup.
[2] All the ingredients used in this formulation meet FDA specification.
[3] The solids content of high fructose corn syrup is approximately 77% with the fructose content being approximately 55% by weight of the solids.
[4] The sorbitol solution is approximately 70% sorbitol.

The suspending system for this acetaminophen containing suspension contains from about 0.1 to about 0.2 grams of xanthan gum per 100 ml of the suspension and about 0.5 to about 1 gram microcrystalline cellulose per 100 ml of the suspension. The preferred xanthan gum for the acetaminophen suspension is Keltrol TM 1000. The preferred microcrystalline cellulose for this suspension is a coprecipitate of in the range of from about 8.3 to about 13.8 percent sodium carboxymethyl cellulose the remainder being cellulose microcrystals, which is commercially available as Avicel TM RC 591.

The acetaminophen added to the suspension should be provided in a particulate form having a particle size range which permits greater than 99 percent of the particle to pass through a 40 mesh screen (U.S. standard screen). The amount of acetaminophen added to the suspension should be sufficient to provide a therapeutic amount of acetaminophen in a convenient dosage unit. The amount of acetaminophen in suspension should be in the range of from about 1 to about 15 grams per 100 ml of suspension.

The preferred sweeteners for acetaminophen suspension are high fructose corn syrup, sorbitol and glycerin. The high fructose corn syrup should be provided as an aqueous solution containing 77% by weight solid. The fructose content of the high fructose corn syrup should be about 55%. The amount of aqueous high fructose corn syrup percent in the acetaminophen suspension should be in the range of from about 20 to about 80 grams per 100 ml of suspension. The sorbitol also should be present as an aqueous solution containing 70% sorbitol by weight. The amount of aqueous sorbitol present in the acetaminophen suspension should be in the range of from about 1 to about 30 grams of sorbitol per 100 mL of the suspension. The amount of glycerin in the acetaminophen suspension should be in the range of from about 1 to about 20 grams of glycerin per 100 mL of the suspension.

The flavoring agent used in the acetaminophen suspension is artificial cherry and grape flavors. The amount of flavoring agent used is an effective amount to provide a palatable flavor to the suspension. Other flavoring agents as previously described may be substituted for this flavoring agent. When artifical cherry and grape flavors are used in an acetaminophen suspension it is preferred that the amount of artifical cherry and grape flavors in the suspension be in the range of from about 0.01 to about 0.5 grams per 100 ml of suspension.

The water added to the suspension should be kept at a minimum, to facilitate masking the bitter taste of acetaminophen. The acetaminophen suspension should contain in the range of from about 10 to 30 grams of water per 100 ml of suspension.

The preservatives present in the acetaminophen suspension are butylparaben and sodium benzoate. Other preservatives could also be used in the suspension. The acetaminophen suspension should contain in the range of from about 0.01 to about 0.05 grams of butylparaben per 100 mL of suspension and in the range of from about 0.1 to about 0.3 grams of sodium benzoate per 100 mL of suspension.

The coloring agent present in the acetaminophen suspension are FD&C Red #40, FD&C Blue #1 and D&C Red #33. Other coloring agents can be used in the acetaminophen containing pharmaceutical suspension. The acetaminophen suspension should contain in the range of from about 0.003 to about 0.0005 grams of FD&C Red #40, FD&C Blue #1 and D&C Red #33 per 100 ml of the suspension.

To prepare the pharmaceutical suspensions provided herein, it is necessary that the microcrystalline cellulose and xanthan gum are adequately dispersed and hydrated to provide the desired rheological characteristic to the suspension. Hydrating the microcrystalline requires high shear mixing to disperse and hydrate the microcrystal cellulose particles. Examples of suitable high shear mixing devices include Scott Turban Mixers, Homogenizers and colloid mills. It is preferred that the microcrystalline cellulose be fully dispersed in a water prior it being mixed with other ingredients. The xanthan gum also should be dispersed in an aqueous suspension, but does not require high shear mixing. Xanthan gum may be added to other aqueous components such as the sugar sweetener and thereafter dispersed by a suitable mixing means such as a propeller mixer.

The dispersed microcrystalline cellulose and xanthan gum should be admixed before the addition of other dry components such as the drug or any buffers, preservatives or colorings. To assure even dispersion of the other ingredients the addition of the other ingredients into the suspension should be performed in a step wise manner. The mixing should be conducted in a manner that does not entrain excess air. However, if excess air is entained in the suspension before the suspension is brought to its final volume it may be deareated to remove entrained air and thereby returned to its normal density. The final volume of the suspension ingredients listed above may not provide a total volume of 100 mL The final volume may be brought to 100 mL by the addition of water or preferably one or more liquid sugar sweeteners. For taste masking purposes it is currently preferred to use liquid sugar sweetener such as high fructose corn syrup or sorbitol to bring the suspension to its final volume.

The flavoring and coloring ingredients added to the mixture should be of the type and amount desired for the particular suspension to meet the preferences dictated by the intended consumer of such suspension e.g. pediatric or adult.

A more detailed example of the preferred process of the invention as carried out with acetaminophen and pseudoephedrine as the active ingredients is provided in the following examples section.

EXAMPLES

The invention will now be illustrated by examples. The examples are not intended to be limiting of the scope of the present invention but read in conjunction with the detailed and general description above, provide further understanding of the present invention and an outline of a preferred process for preparing the compositions of the invention.

EXAMPLE 1:

Acetaminophen Suspension Liquid Dosage Form

This example discloses a pharmaceutical suspension containing acetaminophen and a process for manufacturing this suspension. The ingredients contained in the acetaminophen suspension are as follows:

| Ingredients | g/100 mL |
| --- | --- |
| High Fructose Corn Syrup (HFCS 55%, American Maize) | 76.0 |
| Purified Water USP | 20.0 |
| Sorbitol Solution USP 70% | 20.0 |
| Glycerin USP | 10.0 |
| Xanthan Gum NF (Keltrol 1000, Kelco) | 0.14 |
| Microcrystalline Cellulose NF (Avicel RC 591, FMC) | 0.7 |
| Butylparaben | 0.025 |
| Sodium Benzoate | 0.2 |
| Citric Acid USP (Anhydrous Powder) | 0.075 |
| Acetaminophen USP Powder | 3.2 |
| Coloring | 0.001 |
| Artificial Cherry Flavoring | 0.02 |

MANUFACTURING PROCESS

The acetaminophen suspension was prepared as follows:

1. 10 grams of glycerin USP were poured into an appropriate size stainless steel container. 0.025 grams of butylparaben NF was added to the glycerin USP while mixing using IKA-WERK propeller mixer. The butylparaben NF and glycerin were mixed for 15 to evenly disperse the butylparaben NF. 0.14 grams of xanthan gum NF was then added to the glycerin USP ad butylparaben NF solution. The xanthan gum NF was mixed into solution using the same equipment for 15 minutes or until it was evenly dispersed in the solution.

2. 20.0 grams of purified water USP were placed on appropriate size stainless steel container. 0.7 grams of microcrystalline cellulose NF (Avicel RC 591) was added to the purified water USP while the solution was being constantly mixed with a high shear Scott Turbon mixer. The microcrystalline cellulose was mixed into the purified water USP for 20 minutes or until it was evenly dispersed.

3. The solutions formed by step 1 and step 2 were then admixed together in a 10 gallon stainless steel container. Next 66.0 grams of high fructose corn syrup (55%) and 20.00 grams of sorbitol solution USP (70%) were added to this admixture. The admixture was then mixed for 20 minutes using a high shear Scott Turbon mixer to evenly disperse the various components in the admixture.
4. 0.0125 grams of D&C Red.#40 certified, and 0.075 grams of citric acid USP were then added to the admixture formed by step 3. The colorings and citric acid USP were mixed for 5 minutes using the Scott Turbon mixer or until they were evenly dispersed in the admixture. Next 0.200 grams of sodium benzoate NF were then added to the admixture. The sodium benzoate NF was mixed with the admixture for 25 minutes using the Scott Turbon mixer or until it was evenly dispersed.
5. 10.0 grams of acetaminophen USP powder was added into the admixture produced in step 4. The acetaminophen USP powder was poured into the wet vortex of the admixture which was formed by the high shear Scott Turbon mixer. The speed at which the mixer was running was increased after the introduction of the acetaminophen USP powder to insure even mixing. After the acetaminophen began to disperse, the mixing speed was reduced to avoid entraining air in admixture. The admixture was mixed for 15 minutes or until the acetaminophen was evenly dispersed.
6. 0.02 grams of artificial cherry flavor was added to the admixture formed in step 5. The cherry flavor was mixed into the admixture for 5 minutes or until it was evenly dispersed in the admixture.
7. The final volume of the admixture was adjusted to the final 100 mL volume by adding high fructose corn syrup (55%). The high fructose corn syrup was mixed into the admixture for 15 minutes using a high shear Scott Turbon mixer or until it was evenly dispersed.

EXAMPLE 2

Preparation of Acetaminophen Suspension Liquid

Drop Dosage Form

This example provides a liquid doasage form of acetaminophen which is suitable to be administered in the form of drops. The formulation for this dosage form is as follows:

| Ingredients | g/100 mL |
|---|---|
| High Fructose Corn Syrup (HFCS 55%, American Maize) | 66.0 |
| Purified Water USP | 20.0 |
| Sorbitol Solution USP 70% | 20.0 |
| Glycerin USP | 10.0 |
| Xanthan Gum NF (Keltrol 1000, Kelco) | 0.14 |
| Microcrystalline Cellulose NF (Avicel RC 591, FMC) | 0.7 |
| Butylparaben | 0.025 |
| Sodium Benzoate | 0.2 |
| Citric Acid USP (Anhydrous Powder) | 0.075 |
| Acetaminophen USP Powder | 10.0 |
| Coloring | 0.001 |
| Artificial Grape Flavoring | 0.0325 |

MANUFACTURING PROCESS

The ingredients were mixed together following the procedure set forth in Example I. However, grape flavor was substituted for the cherry flavor used in Example I. Additionally, the coloring agents were changed to provide a purple color for the drops by using 0.001 grams D&C Red #33 and 0.00015 grams FD&C Blue #1.

The scope of the present invention is not limited by the description, examples and suggested uses herein and modifications can be made without departing from the spirit of the invention. For example, additional medicaments may be added to the aqueous suspension to provide combination medications. Further, the pharmaceutical suspension of the invention may be utilized for non-medicament ingredients including nutrients such as vitamins and minerals.

Application of the compositions and methods of the present invention for medical and pharmaceutical uses can be accomplished by any clinical, medical and pharmaceutical methods and techniques as are presently or prospectively known to those skilled in the art. Thus it is intended that the present invention cover the modifications and variations of the invention provided that they come within the scope of the appended claims and their equivalents.

What is claimed is:

1. A pharmaceutical suspension comprising a therapeutic amount of pharmaceutical active selected from the group consisting of acetaminophen, famotidine, pseudoephedrine hydrochloride, chlorpheniramine maleate, astemizole, dextromethorphan hydrobromide, quaifenesin, diphenhydramine hydrochloride, loperamide hydrochloride, simethicone, antacids, and combinations thereof; a suspending system consisting essentially of a suspension stabilizing effective amount of xanthan gum in the range of about 0.12 to about 0.2 gram per 100 mL of the suspension and microcrystalline cellulose in the range of about 0.5 to about 1.0 gram per 100 mL of the suspension; water and an effective amount of a sweetening agent and a flavoring agent to provide a palatable taste to said pharmaceutical suspension.

2. The pharmaceutical suspension of claim 1 wherein the sweetening agent is selected from the group consisting of xylose, ribose, glucose, mannose, galactose, fructose, dextrose, sucrose, maltose, partially hydrolyzed starch solids, partially hydrolyzed corn syrup solids, sorbitol, xylitol, mannitol, glycerin, aspartame, sucralose, cyclamates, saccharin and mixtures thereof.

3. The pharmaceutical suspension according to claim 1 wherein the weight ratio of xanthan gum to microcrystalline cellulose is about a 1:5 ratio.

4. The pharmaceutical suspension according to claim 1 wherein the sweetening agent and flavoring agent comprises from about 40 to 85 grams per 100 mL suspension.

5. The pharmaceutical suspension of claim 1 wherein the amount of xanthan gum present is in the range of from 0.13 to 0.15 gram per 100 mL of suspension and the amount of microcrystalline cellulose present is in the range of from 0.65 to 0.75 gram per 100 mL of suspension.

6. The pharmaceutical suspension of claim 1 wherein the pharmaceutical active is acetaminophen.

7. A pharmaceutical suspension consisting essentially of:

|  | g/100 mL |
| --- | --- |
| Xanthan Gum | 0.1–0.2 |
| Microcrystalline Cellulose | 0.5–1 |
| Acetaminophen | 1–15 |
| High Fructose Corn Syrup | 20–80 |
| Sorbitol Solution USP | 1–30 |
| Glycerin USP | 1–20 |
| Flavoring | 0.01–0.5 |
| Purified Water USP | 10–30 |
| Coloring | 0.003–.0005 |
| Sodium Benzoate NF | 0.1–0.3 |
| Butylparaben | 0.01–0.05 |
| Citric Acid USP | 0.05–0.18. |

8. A pharmaceutical suspension consisting essentially of:

|  | g/100 mL |
| --- | --- |
| Xanthan Gum | 0.13–0.15 |
| Microcrystalline Cellulose | 0.65–0.75 |
| Acetaminophen | 8–12 |
| High Fructose Corn Syrup | 60–75 |
| Sorbitol Solution USP | 15–25 |
| Glycerin USP | 8–12 |
| Flavoring | 0.01–0.1 |
| Purified Water USP | 15–25 |
| Coloring | 0.0005–.002 |
| Sodium Benzoate NF | 0.15–0.3 |
| Butylparaben | 0.02–0.03 |
| Citric Acid USP | 0.06–0.12. |

9. A pharmaceutical suspension consisting essentially of:

|  | g/100 mL |
| --- | --- |
| High Fructose Corn Syrup | 76.0 |
| Purified Water USP | 20.0 |
| Sorbitol Solution USP 70% | 20.0 |
| Glycerin USP | 10.0 |
| Xanthan Gum NF | 0.14 |
| Microcrystalline Cellulose NF | 0.7 |
| Butylparaben | 0.025 |
| Sodium Benzoate NF | 0.2 |
| Citric Acid USP (Anhydrous Powder) | 0.075 |
| Acetaminophen USP Powder | 3.2 |
| Coloring | 0.001 |
| Flavoring | 0.0325. |

10. A method for forming an aqueous pharmaceutical suspension comprising the steps of:

a) dispersing microcrystalline cellulose in an aqueous solution to form a first liquid dispersion;
b) dispersing xanthan gum in a liquid solution to form a second liquid dispersion;
c) admixing said first liquid dispersion and said second liquid dispersion with a pharmaceutical active selected from the group consisting of acetaminophen, famotidine, pseudoephedrine hydrochloride, chlorpheniramine maleate, astemizole, dextromethorphan hydrobromide, guaifenesin, diphenhydramine hydrochloride, loperamide hydrochloride, simethicone, antacids and combinations thereof to form an aqueous pharmaceutical suspension, wherein the concentration of microcrystalline cellulose and xanthan gum in the aqueous suspension are in the range of from about 0.5 to about 1.0 gram of microcrystalline cellulose per 100 mL of aqueous suspension and in the range of from about 0.1 to about 0.2 gram of xanthan gum per 100 mL of the aqueous pharmaceutical suspension.

11. A method for preparing an aqueous pharmaceutical suspension composition from the following ingredients comprising the steps of:

a) dispersing xanthan gum in an aqueous sugar sweetener to form a first liquid dispersion;
b) dispersing microcrystalline cellulose in water to form a second liquid dispersion;
c) admixing said first liquid dispersion and said second liquid dispersion with a water soluble pharmaceutical active selected from the group consisting of acetaminophen, famotidine, pseudoephedrine hydrochloride, chlorpheniramine maleate, astemizole, dextramethorphan hydrobromide, quaifenesin, diphenhydramine hydrochloride, loperamide hydrochloride, simethicone, antacids, and combinations thereof and an effective amount of preservatives, colorings and flavorings until uniformly dispersed to form a third liquid dispersion; and wherein the concentration of the ingredients in 100 mL is: xanthan gum 0.1 to 0.2 gram; sugar sweetener 40 to 85 grams; microcrystalline cellulose 0.5 to 1 gram; water 30 to 55 grams; and water soluble pharmaceutical up to 40 grams.

12. The method of claim 11 wherein the sugar sweetener is selected from the group consisting of xylene, ribose, glucose, mannose, glactose, fructose, dextrose, sucrose, maltose, partially hydrolyzed starch solids, partially hydrolyzed corn syrup solids, sorbitol, xylitol, mannitol, and glycerin.

* * * * *